(12) United States Patent
Fontana

(10) Patent No.: US 8,517,996 B2
(45) Date of Patent: Aug. 27, 2013

(54) CANNULA FOR DISPENSING FLUID PRODUCTS, PARTICULARLY FOR VAGINAL AND RECTAL APPLICATIONS

(75) Inventor: Antonio Fontana, Carpi (IT)

(73) Assignee: Lameplast S.p.A., Modena (IT)

( * ) Notice: Subject to any disclaimer, the term of this patent is extended or adjusted under 35 U.S.C. 154(b) by 244 days.

(21) Appl. No.: 13/148,355

(22) PCT Filed: Feb. 4, 2010

(86) PCT No.: PCT/IB2010/000217
§ 371 (c)(1),
(2), (4) Date: Aug. 8, 2011

(87) PCT Pub. No.: WO2010/089653
PCT Pub. Date: Aug. 12, 2010

(65) Prior Publication Data
US 2011/0313366 A1 Dec. 22, 2011

(30) Foreign Application Priority Data
Feb. 9, 2009 (IT) .............................. M02009A0031

(51) Int. Cl.
*A61M 5/32* (2006.01)

(52) U.S. Cl.
USPC ............ 604/193; 206/229; 206/364; 604/279

(58) Field of Classification Search
USPC ........... 604/16, 193, 194, 219, 279, 285–288; 206/229, 363–367
See application file for complete search history.

(56) References Cited

U.S. PATENT DOCUMENTS

| 2,725,057 A | 11/1955 | Lockhart |
| 3,882,866 A | 5/1975 | Zackheim |
| 2004/0260252 A1 | 12/2004 | DiPiano et al. |

FOREIGN PATENT DOCUMENTS

| EP | 1 518 574 | 3/2005 |
| FR | 1.600.637 | 7/1970 |
| WO | WO 2004/014476 | 2/2004 |

OTHER PUBLICATIONS

International Search Report issued on May 25, 2010 in International Application No. PCT/IB2010/00217.

*Primary Examiner* — Emily Schmidt
(74) *Attorney, Agent, or Firm* — Stein IP, LLC

(57) ABSTRACT

A cannula (1) for dispensing fluid products, particularly for vaginal and rectal applications, comprises: a tubular body (2) for containing a fluid product (P), having a first extremity (2a), at which a dispenser opening (3) is formed, and a second open extremity (2b), opposed to the first extremity (2a). A closing body (5) which is associable with the tubular body (2) to close the second extremity (2b). The closing body comprises a first element (6) at least partially insertable through the second extremity (2b) and suitable for acting as a sliding piston inside the tubular body (2), and a second annular body, that functions a tamper indication seal. A cover cap (4) which can be fitted on the tubular body (2) to close the dispenser opening (3) and which is made in a single body piece. Longitudinal score lines divide the cover cap into a plurality of first sections and a single second section. Fold lines extend longitudinally along the first sections. Single second section is torn away from the body along the weakened score lines, and the first sections are bent over the fold lines to form a push rod of reduced transverse dimensions. Push rod is insertable into tubular body to slide first section of closing cap along interior of cannula to discharge fluid product.

7 Claims, 4 Drawing Sheets

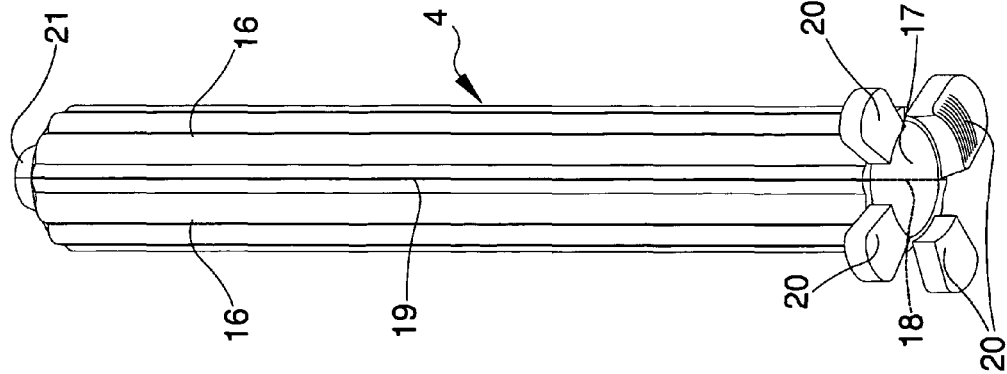
Fig. 5
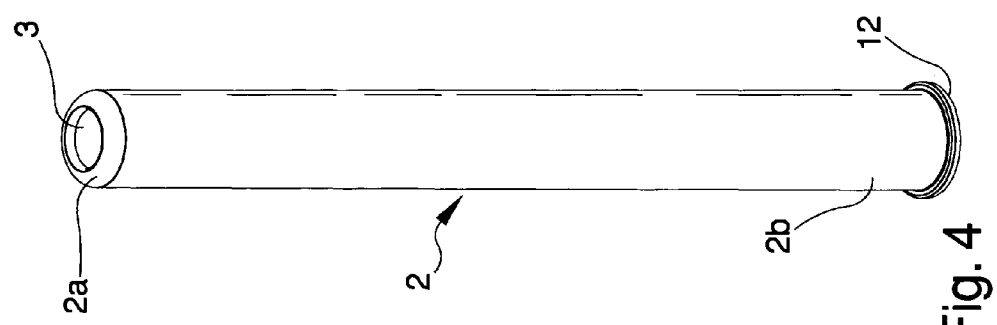
Fig. 4
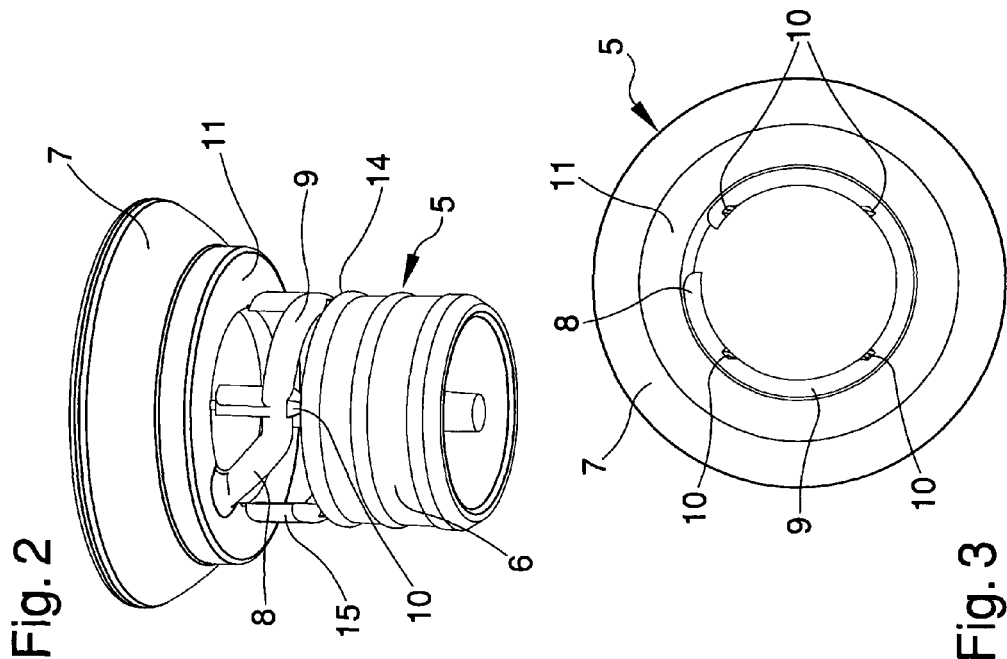
Fig. 2
Fig. 3

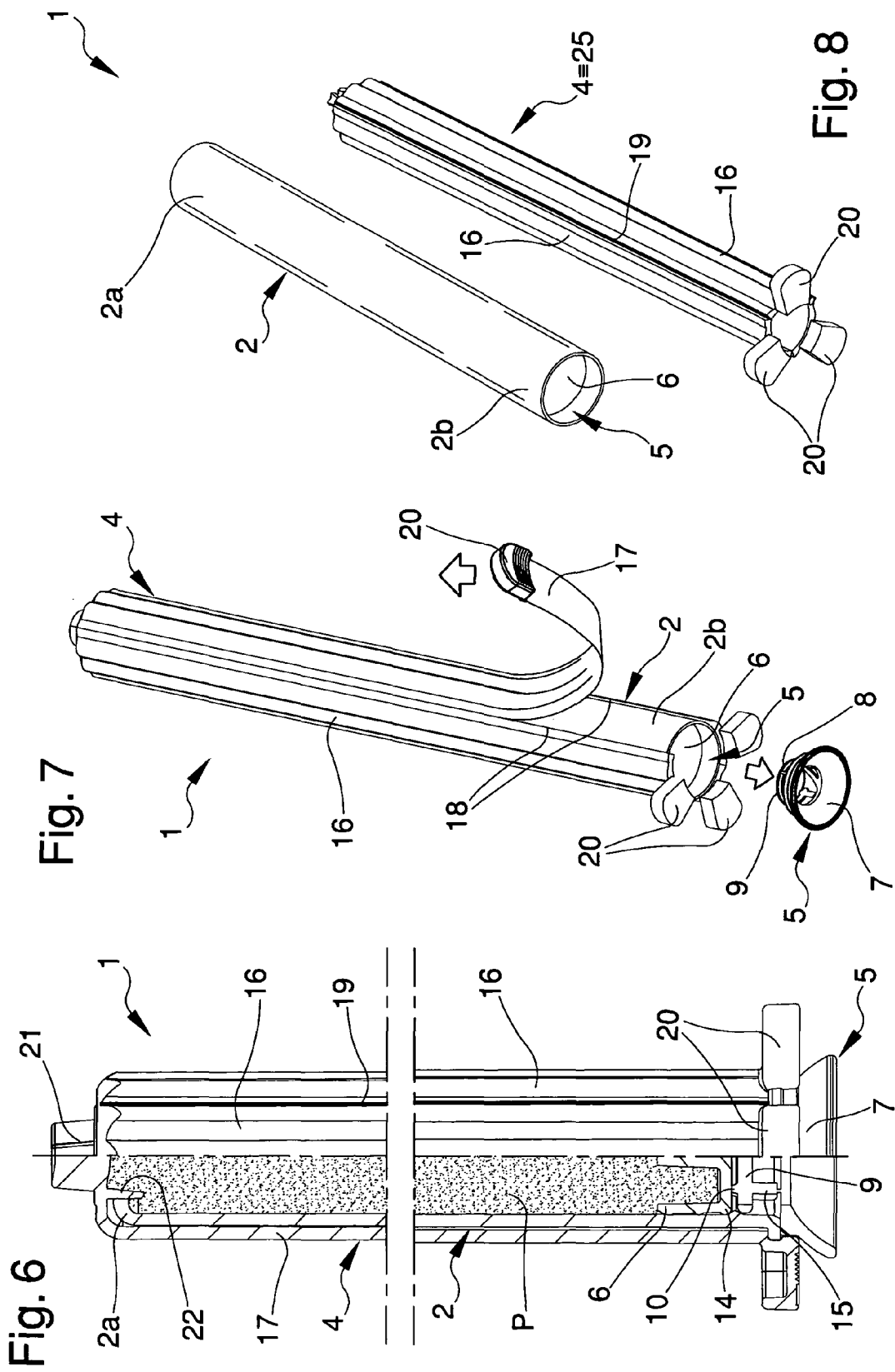

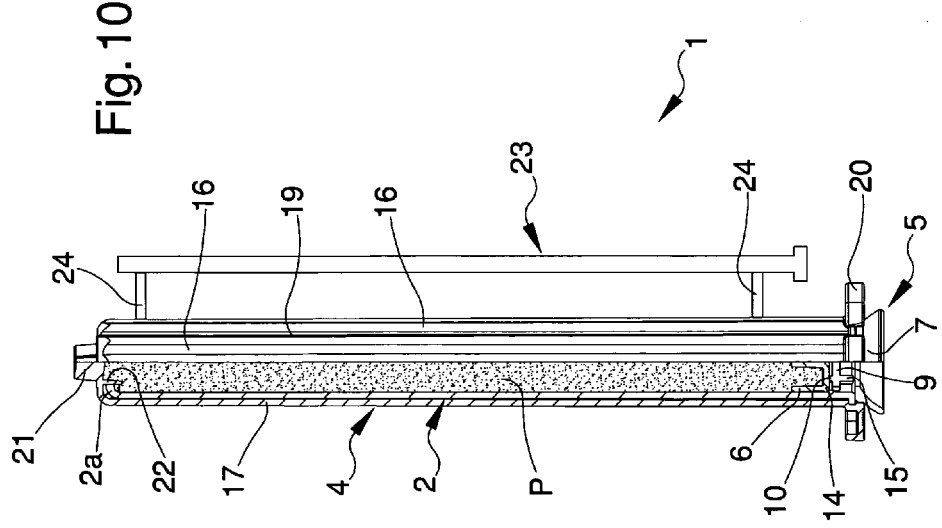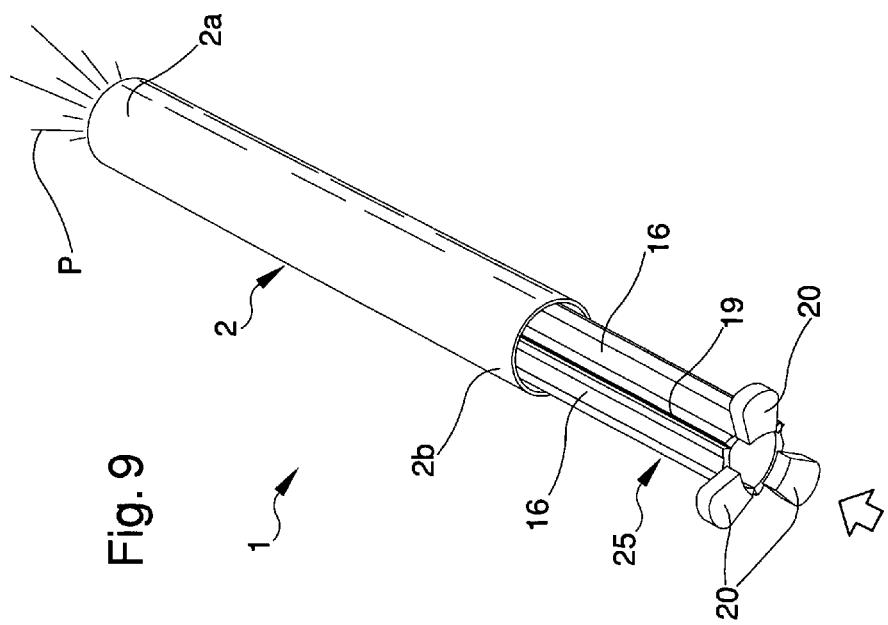

CANNULA FOR DISPENSING FLUID PRODUCTS, PARTICULARLY FOR VAGINAL AND RECTAL APPLICATIONS

CROSS-REFERENCE TO RELATED APPLICATIONS

This application claims the benefit of PCT International Patent Application No. PCT/IB2010/000217, filed Feb. 4, 2010, and Italian Patent Application No. MO2009A000031, filed Feb. 9, 2009, in the Italian Intellectual Property Office, the disclosures of which are incorporated herein by reference.

BACKGROUND OF THE INVENTION

1. Field of the Invention

The present invention relates to a cannula for dispensing fluid products, particularly for vaginal and rectal applications.

2. Description of the Related Art

Cannulas are known for dispensing medical fluid products which are used, in particular, for vaginal and rectal applications and which are generally sold in packs together with tubes or bottles containing the fluid products.

The known cannulas are composed of a cylinder suitable for containing the product and inside which is a piston integral with the extremity of a push rod.

The cylinder has an open extremity that can be coupled with the dispenser mouth of the tube, to introduce the quantity of product to be applied into the cylinder, and through which the introduced product is dispensed.

The opposite extremity of the cylinder is closed by a bottom wall which has a hole, through which the push rod is inserted for slide movement within the cylinder. The bottom wall acts as a piston stop element to prevent its withdrawal.

The dispensing of the product introduced into the cannula occurs by moving the push rod, to slide the piston towards the open extremity of the cylinder.

These known cannulas have a number of drawbacks. To illustrate they are rather complex in terms of structure and assembly and that, being for hygienic reasons of the single-use type and requiring a push rod for each cylinder, they produce a considerable waste of materials.

To overcome such drawbacks, cannulas are known composed of one cylinder, which has the opposite extremities open and inside which a piston is fitted in a sliding manner, and a push rod, separate from the piston, is removably coupled to same.

At the opposite extremities of the cylinder undercuts or stop shoulders are obtained or formed for stopping the sliding of the piston and preventing the piston from coming out of the cylinder as a result of the action of the push rod.

These latter cannulas can be sold in packs containing a single push rod, a plurality of empty single-use cylinders to be used for the different applications, and one or more product tubes.

In this case, one of the two extremities of the cylinders can be coupled with the dispenser mouth of the tube for the introduction of the product into the cylinders, while the opposite extremity acts as a passage for the push rod.

These latter known cannulas have made it possible to curb the consumption of materials, for the same push rod, in fact, can be used with a plurality of cylinders.

Nevertheless, these cannulas are not without drawbacks as well, tied above all, to the need to use one or more tubes of product to load the cylinders before use.

To overcome this drawback, an alternative type of so-called "pre-filled" cannula is known, wherein the cylinder, at the time of purchase, is already filled with the product to be applied and which has closing caps, at the two opposite extremities which are removed at the time of use.

The pre-filled cannulas are not without drawbacks however, for they are of a rather complex construction, and they have rather high production costs and production cycles.

The cylinders, the pistons, the push rods and the closing caps in fact are normally made by molding polymer materials, in several pieces (at least five), separate from one another and subsequently assembled. This involves the design and building of various molds and laborious assembly operations which negatively affect the production costs and times of the cannulas, as well as producing considerable and costly material waste.

From the patent WO 2004/014476 on the other hand a particular type of pre-filled cannula is known in which the cylinder and the piston are made in a single body piece and, at an extremity of the cylinder, are joined together along a connection line with tearable weakened section.

The opposite extremity of the cylinder is closed by means of a tear-off film.

This particular type of pre-filled cannula also has a number of drawbacks. For example the fabrication of the piston in a single body piece with the cylinder is considerably complicated and hard to achieve in practice.

It should also be considered that big difficulties of a practical-manufacturing nature are encountered because of the use of the tear-off film.

Another type of pre-filled cannula is on the other hand known from EP 1 518 574 and comprises a push rod that can be extended by means of a telescopic rod system between a retracted configuration and an elongated configuration.

The push rod is made in a retracted configuration together with the cylinder at an extremity of same.

The opposite extremity of the cylinder is closed by a cover cap made to fit over the cylinder permanently along its entire length until it joins at the base of the push rod.

The cannula or cylinder described in EP 1 518 574 also suffers various drawbacks. The push rod involves the manufacture and the assembly of a plurality of telescopic elements, with consequent increase in time and costs of designing, producing and assembly, as well as the waste of a considerable quantity of materials.

SUMMARY OF THE INVENTION

The main aim of the present invention is to provide a cannula for dispensing fluid products, particularly for vaginal and rectal applications, which is structurally and constructively very simple, that reduces production time and costs, and limits the waste of materials.

A further object of the present invention is to provide a cannula for dispensing fluid products, particularly for vaginal and rectal applications, which is of compact dimensions, is easy to handle, and which can be immediately used by users.

Another object of the present invention is to provide a cannula for dispensing fluid products, particularly for vaginal and rectal applications, which overcomes the mentioned drawbacks of the known art in an easy, effective, and low cost manner.

The above objects are achieved by the present cannula for dispensing fluid products, particularly for vaginal and rectal applications, comprising a tubular body for containing a fluid product, the tubular body having a first extremity, at which a dispenser opening is located, and a second open extremity, opposed to the first extremity, a closing body which is associable with said tubular body to close said second extremity. The closing body includes a first cylindrical element partially insertable through said second extremity and serving as a sliding piston inside said tubular body. A unitary cover cap, which can be fitted on said tubular body, closes said dispenser opening and can be converted into at least a push rod insertable in said tubular body to force the first cylindrical element to slide along the interior of said tubular body and discharges the fluid product through the dispensing opening in the tubular body of the cannula.

The cover cap, after removal from the tubular body of the cannula, is converted into a push rod for sliding a piston, which corresponds to the first part of the closing body, through the interior of the cannula to discharge the product contained therein. Weakened, or score, lines divide the cover cap into several longitudinal sections. Removal of one section, by tearing same away from the body of the cover cap, leaves an elongated opening, and several other sections.

Spaced fold lines also extend longitudinally along the cover cap. Several of the sections remaining in the cover cap may be folded over, or bent, about the fold lines. The transverse dimensions of the cover cap is reduced so that the cover cap may be inserted into an opening in an extremity of the cannula, to serve as a push rod for the piston to slide same within the cannula to discharge the fluid product contained therein. Gripping fins are formed at the lower end of the longitudinal sections to facilitate removal of the longitudinal sections.

The removal of the section defined by the weakened, or score, lines leaves an opening in the body of the cover cap, and increases its flexibility. The cover cap may be squeezed by the user to reduce its dimension to the desired extent, or the cover cap may be deformed inwardly to fit within the opening in the cannula as it is forced therein with gentle pressure exerted by the user.

BRIEF DESCRIPTION OF THE DRAWINGS

Other characteristics and advantages of the present invention will become more evident from the description of some preferred, but not sole, embodiments of a cannula for dispensing fluid products, particularly for vaginal and rectal applications, illustrated purely as an example but not limited to the annexed drawings in which:

FIG. 2 is an axonometric view of the closing body of the cannula of FIG. 1;

FIG. 3 is a section view along the plane III-III of FIG. 1;

FIG. 4 is an axonometric view of the tubular body of the cannula of FIG. 1;

FIG. 5 is an axonometric view of the cover cap of the cannula of FIG. 1;

FIG. 6 is a section view of the cannula of FIG. 1 in packaging configuration;

FIGS. 7-9 show, in a sequence of axonometric views, the use method of the cannula of FIG. 1;

FIG. 10 is a section view of a second embodiment of the cannula according to the invention in packaging configuration.

DETAILED DESCRIPTION OF THE EMBODIMENTS

Figure 1:
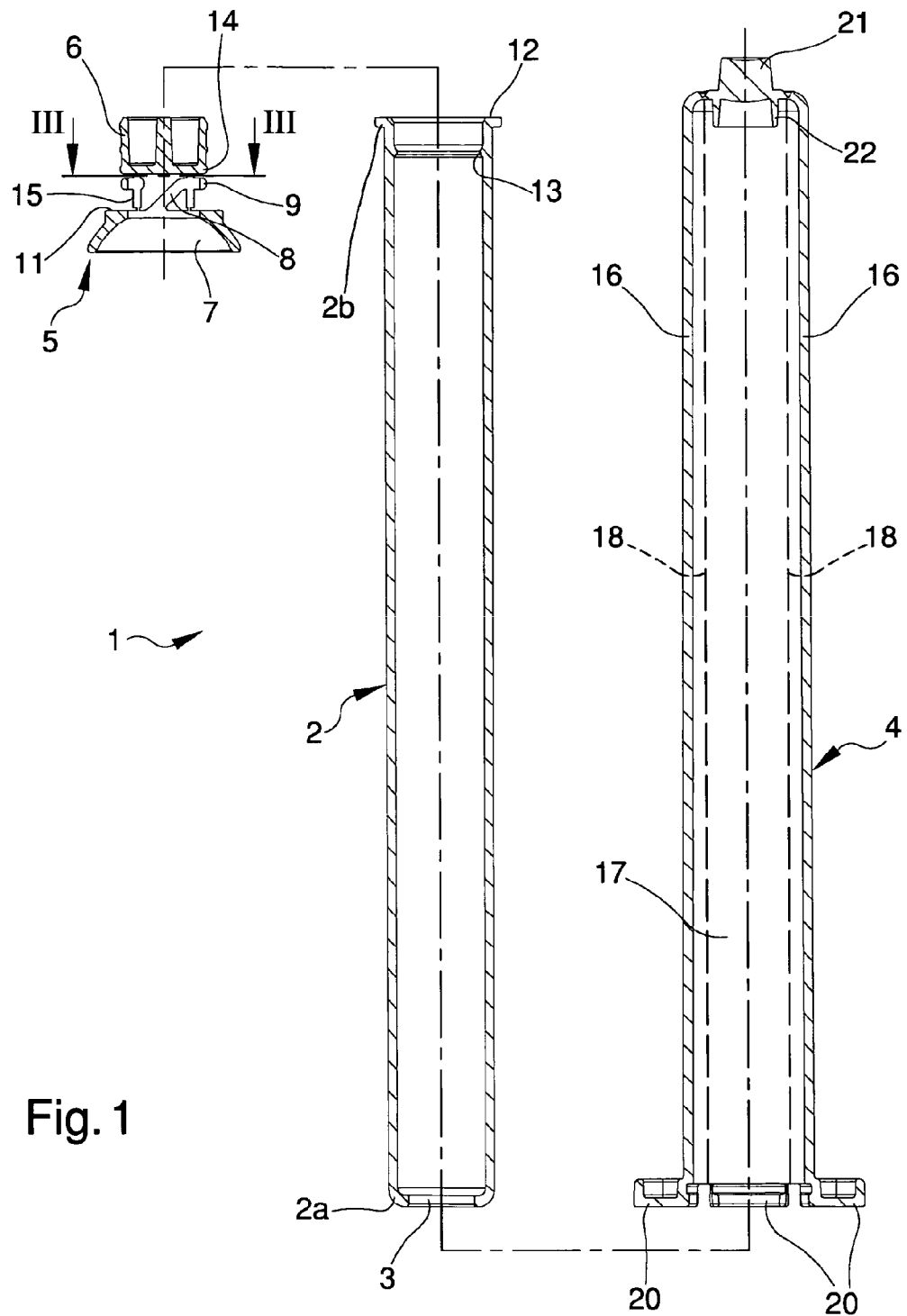
FIG. 1 is an exploded and section view of a first embodiment of the cannula according to the invention.

With particular reference to the embodiment of FIGS. 1 to 9, depict a cannula for dispensing fluid products, particularly for vaginal and rectal applications; the cannula is configured in accordance with the principles of applicant's invention.

In this application the term fluid products include not only liquid products but also viscous products, in the form of paste and gel, and powdered products, in particular very fine powders distinguished by great flowability.

Cannula 1 comprises a tubular body 2 which contains the fluid product P.

The tubular body 2 is shaped like a straight cylinder and has a first extremity 2a at which a dispenser opening 3 is formed.

In the embodiment of the figures from 1 to 9 there is only one dispenser opening 3 which extends crossways to the longitudinal direction of the tubular body 2.

Alternative embodiments of the invention are, however, possible, in which several dispenser openings 3 are provided and/or in which these openings are obtained, or formed, on the side surface of the first extremity 2a.

On the opposite side with respect to the first extremity 2a. The tubular body 2 has a second open extremity 2b on the opposite end, remote from first extremity 2a.

The cannula 1 also comprises a cover cap 4, which is made separate from the tubular body 2, and which can be fitted on body 2 to close the dispenser opening 3.

To close the second extremity 2b, on the other hand, the cannula 1 comprises a closing body 5, formed separately from the tubular body 2.

The closing body 5 comprises a first element 6, and a second element 7 joined along tearable connection members 8, 9, 10. Elements 6, 7 and connection members 8, 9 and 10 are formed on a unitary molding.

Second element 7 has a substantially annular shape and can be torn off the first element 6 to act as an anti-tampering seal, to indisputably indicate that the cannula 1 has actually been opened by a user.

The first element 6, on the other hand, has a substantially cylindrical shape and can be inserted snugly through the second extremity 2b to act as a piston slidable inside the tubular body 2 once the second element 7 has been torn off.

For this purpose, the cannula 1 has temporary retention members 11, 12, 13, 14 suitable for retaining the closing body 5 in a packaging configuration in which the first element 6 is inserted into the tubular body 2 near to the second extremity 2b.

The temporary retention members 11, 12, 13, 14, comprise a shoulder edge 11, which is obtained or formed on the second element 7, and a corresponding locator edge 12, which is obtained around the second extremity 2b of the tubular body 2. The locator edge 12 engages the shoulder edge 11 to act as a stop and prevent further insertion of the closing body 5 into the tubular body 2.

The temporary retention members 11, 12, 13, 14 also comprise a stop tooth 13, which is obtained in a centripetal overhang on the inner surface of the tubular body 2, and a corresponding locator surface 14, which is obtained or formed on the first element 6. The first element 6 is engaged against the stop tooth 13 to prevent the withdrawal of the first element 6 from the tubular body 2.

The tearable connection members 8, 9, 10 comprise a removal arm 8, 9 stably joined to the second element 7 and connected to the first element 6 by the interposition of a plurality of weakened-section connection points 10.

The removal arm 8, 9, consists of a first portion 8, which extends substantially obliquely from the second element 7, and of a second portion 9, with substantially annular conformation, which develops along a plane substantially at right angles to the longitudinal direction of the tubular body 2. The connection points 10 are distributed along such plane.

Stiffening bridges 15 are also provided which permit transmitting thrust forces from the second element 7 towards the first element 6. The bridges extend between second portion 9 and first element 6 of closing body 5.

Cover cap 4 is made in a single body piece which can be converted into push rod 25. Push rod 25 is inserted into tubular body 2 to slide the first element 6 along the tubular body 2 and dispensing fluid product P through the dispenser opening 3.

For this purpose, cover cap 4 is split into a plurality of first longitudinal sections 16 and a second longitudinal section 17 which can be torn away from the first longitudinal sections 16.

The second longitudinal section 17, in particular, is joined to the first longitudinal sections 16 along weakened-section longitudinal connection lines 18 that extend substantially the entire length of cannula 1.

The first longitudinal sections 16, on the other hand, can be folded on themselves along longitudinal folding lines 19 that extend substantially along the entire length of cannula 1.

Once the second longitudinal section 17 has been torn off, or torn away, the first longitudinal sections 16 are folded on themselves, to define the push rod 25.

The transversal dimensions of the first longitudinal sections 16 folded on themselves are in fact considerably less than the diameter of the cover cap 4 and consequently allow the insertion of tubular body 2 to push the first element 6 therethrough.

In the embodiment shown in the figures from 1 to 9, therefore, the push rod 25 coincides with at least a part of the cover cap 4.

To make gripping by the user easier, the first longitudinal sections 16 and the second longitudinal section 17 have gripping fins 20 obtained, or formed, at the extremity of the cover cap 4 corresponding to the second extremity 2b of the tubular body 2.

In particular, the gripping fins 20 of the first longitudinal sections 16 are distributed in an asymmetric way, as is clearly visible in the FIG. 5.

At the opposite extremity, the cover cap 4 has an interior wall 21 which is substantially transversal to the longitudinal direction of the tubular body 2 and which fits over the first extremity 2a.

Cover cap 4 further comprises an inner shutter body 22 which can be inserted snugly into the dispenser opening 3.

Both the wall 21 and the shutter body 22 are part of the second longitudinal section 17, of cover cap 4 and can be torn off, or away, from the first longitudinal sections 16.

The operation of the cannula 1 shown in the figures from 1 to 9 is the following.

The cannula 1 is made of three separate pieces (tubular body 2, cover cap 4 and closing body 5) assembled together.

To make up the cannula 1, cover cap 4 is, first of all, fitted on the tubular body 2. The tubular body 2 is pre-filled with the fluid product P and then the second extremity 2b is closed or sealed by the closing body 5.

The insertion of the closing body 5 in the tubular body 2 is achieved by pushing the second or annular element 7 until the shoulder edge 11 abuts the locator edge 12 and the first element 6 is blocked on the stop tooth 13. In this phase, the thrust force is transmitted from the second element 7 to the first element 6 through the stiffening bridges 15.

The cannula 1 is then distributed or sold in the market in the packaging configuration shown in FIG. 6, with the tubular body 2 pre-filled, covered by the cover cap 4, and sealed by the closing body 5.

At the time of use, the user removes the second element 7 and the cover cap 4 from the tubular body 2 (FIG. 7).

For this purpose, it is lined that the removal of the second element 7 takes place simply by moving the second element 7, or tamper indicating seal, away from the second extremity 2b of cannula 1.

Such movement also drags outwards the removal arm 8, 9 which, by means of the first portion 8, is firmly joined to the second element 7.

The particular conformation of the removal arm 8, 9 thus allows tearing the connection points 10 in a sequential way. In other words, the annular shape of the second portion 9 causes the connection points 10 to be placed under tension and torn one after the other, and not all at the same time.

Consequently, the force transmitted to the first element 6 is very limited and is easily discharged onto the stop tooth 13.

The removal of the cover cap 4, on the other hand, occurs by tearing second longitudinal section 18 along the longitudinal connection lines 18, as shown in FIG. 7.

All the user has to do is tear the second longitudinal section 17 by levering the corresponding gripping fin 20.

The second longitudinal section 17, in practice, also acts as an anti-tampering seal as it indisputably shows whether the cannula 1 has been opened. Once torn, section 17 can be discarded as waste.

The first longitudinal sections 16, on the other hand, are then folded on themselves along the longitudinal folding lines 19 (FIG. 8) to form a push rod 25 to push the first element 6, in a sliding manner, along the tubular body 2 (FIG. 9).

The particular asymmetric distribution of the gripping fins 20 easily permits folding the first longitudinal sections 16 superimposing, at least in part, the torn flaps, to facilitate the formation of the push rod 25 of reduced dimension its insertion into the tubular body 2.

In an alternative embodiment of the invention shown in the FIG. 10, the cannula 1 consists of a tubular body 2, a closing body 5 and a cover cap 4 substantially identical to those of the figures from 1 to 9. However in this embodiment the push rod 25 does not correspond or coincide with the cover cap 4, but consists of an elongated slat 23 joined to the cover cap 4 by interposition of a pair of tearable connection segments 24.

In the embodiment of FIG. 10, as well as the preferred embodiment of FIGS. 1-9, cannula 1 is made in just three separate pieces. However, it is not the first longitudinal sections 16 of the cover cap 4 that act or convert a push rod 25, but the elongated slat 23.

The operation of this alternative embodiment is substantially the same as that previously described and illustrated. The difference is that before use, the elongated slat 23 must be separated from the cover cap 4, by tearing connection segments 24, in order to use slot 23 as a push rod 25 to slide first element 6 along the interior of tubular body 2.

It has, in practice, been found that the invention, as described, achieves the intended objects or results.

In this respect, it is underlined that the present cannula for the dispensing of fluid products, particularly for vaginal and rectal applications, can be fabricated by assembly of just three components, permitting a considerable reduction in production times and costs, as well as minimizing the waste of material.

It is further pointed out that, thanks to a simple and compact structure, the cannula, according to the present invention, has low overall dimensions and is particularly simple and handy to use.

Various modifications and revisions to applicant's cannula may occur to the skilled artisan. Consequently, the appended claims should be construed in a manner consistent with the spirit and scope of the applicant's invention, and should not be narrowly construed in accordance with their literal terms.

The invention claimed is:

1. A cannula for dispensing fluid products, particularly for vaginal and rectal applications, said cannula including a tubular body for containing a fluid product, said tubular body having a first extremity with a dispenser opening and a second extremity with another opening at the opposite end of said body, a closing element including a cylindrical body insertable through said second extremity to function as a sliding piston inside said tubular body, a cover cap which fits over said tubular body of said cannula to close said dispenser opening, score lines extending longitudinally along the length of said cover cap to divide same into longitudinal sections, one of said longitudinal sections being removed from said cover cap by tearing same along said score lines, fold lines joining the remaining longitudinal sections to said cover cap, and said remaining longitudinal sections being folded over said fold lines to reduce the transverse dimensions of said cover cap after the removal of said longitudinal section, thereby allowing same to fit into said second extremity of said cannula and serve as a push rod for said cylindrical body of said closing element.

2. The cannula according to claim 1 wherein said cover cap, said cylindrical body, and said cannula are molded separately.

3. The cannula according to claim 1 wherein gripping fins are provided at the end of the longitudinal sections to facilitate the removal thereof from the body of the cover cap.

4. The cannula according to claim 1, wherein said cover cap comprises at least a transverse bottom wall substantially fittable in front of said first extremity.

5. The cannula according to claim 1, wherein said cover cap comprises at least a shutter body insertable into said dispenser opening of said cannula.

6. The cannula according to claim 1, wherein said push rod comprises at least an elongated slat joined to said cover cap by a tearable connection segment.

7. A method of converting a cover cap into a push rod for a cannula for dispensing fluid products, the cannula including a tubular body for containing a fluid product, said body having a first extremity with a dispenser opening and a second extremity with another opening at the opposite end of said body, a closing element with a cylindrical body, a cover cap that fits over the tubular body of said cannula, the method comprising the steps of:

1) forming longitudinal score lines along the said cover cap to divide the cap into a plurality of longitudinal sections, 2) forming fold lines along said cover cap along several of the longitudinal sections, 3) removing one of said longitudinal sections by tearing same away from the body of said cover cap along said score lines, to form an opening in said cover cap, 4) bending several of the remaining longitudinal sections over said fold lines, thereby 5) reducing the transverse dimensions of said cover cap so that said cap is inserted into said second extremity of said cannula to contact the body of said closing element, and 6) sliding the cylindrical body within the tubular body of the cannula to dispense the fluid product.

* * * * *